US006554967B1

(12) United States Patent
Tanaka et al.

(10) Patent No.: US 6,554,967 B1
(45) Date of Patent: Apr. 29, 2003

(54) METHOD OF REFINING DIHYDROXYARYL COMPOUND

(75) Inventors: Shuji Tanaka, Ube (JP); Genji Koga, Ube (JP); Hiroshi Kofuji, Ube (JP); Tetsuro Kawashita, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 09/575,886

(22) Filed: May 22, 2000

(30) Foreign Application Priority Data

May 25, 1999 (JP) .......................... 11-144562

(51) Int. Cl.[7] .................. B01D 3/34; C07C 37/74; C07C 39/08
(52) U.S. Cl. .................. 203/86; 203/91; 203/92; 203/95; 568/753; 568/764; 202/267.1
(58) Field of Search .................. 203/95, 86, 100, 203/92, 91, DIG. 7; 202/267.1; 568/752, 753, 764; 159/DIG. 15

(56) References Cited

U.S. PATENT DOCUMENTS

| 3,860,494 A | * | 1/1975 | Hickman | ............... 122/35 |
| 4,308,112 A | | 12/1981 | Jupe et al. | ............... 203/80 |
| 4,350,573 A | * | 9/1982 | Kritzler et al. | ........ 202/267.1 |
| 4,362,604 A | * | 12/1982 | Jupe et al. | ............... 203/75 |
| 5,502,249 A | * | 3/1996 | Fillers et al. | ............... 203/28 |

OTHER PUBLICATIONS

Partial European Search Report.

* cited by examiner

Primary Examiner—Virginia Manoharan
(74) Attorney, Agent, or Firm—Morgan, Lewis & Bockius LLP

(57) ABSTRACT

A refined dihydroxyaryl compound, for example, catechol, having a high degree of purity and a very low metal content is produced by evaporating a starting dihydroxyaryl compound in a distillation column, condensing the vapor fraction in a condenser connected to a top outlet of the distillation column, and collecting the condensed fraction from the condenser into a storage tank through a conduit, wherein the condenser and optionally the conduit and/or the storage tank have inside surfaces thereof formed from a metal material containing at least 25% by weight of nickel, and the condensed dihydroxyaryl compound fraction is brought into contact with the specific nickel (25% or more)-containing metal inside surface.

17 Claims, No Drawings

METHOD OF REFINING DIHYDROXYARYL COMPOUND

BACKGROUND OF THE INVENTION

1. Field of the Invention

The present invention relates to a method of refining a dihydroxyaryl compound. More particularly, the present invention relates to a method of refining a dihydroxyaryl compound by using a distillation apparatus.

Among the high purity dihydroxyaryl compounds which can be refined by the method of the present invention, catechol has a chelate-forming property with various types of metal, and thus is useful as an impurity metals-removing agent for a base plate in procedures for producing a base plate of electronic devices.

2. Description of the Related Art

It is known that dihydroxyaryl compounds are refined by distillation to increase the degree of purity of the dihydroxyaryl compounds. In the conventional refining method, the distillation is carried out by using a distillation apparatus comprising an evaporating apparatus, a condenser connected to a top portion of the evaporating apparatus, and a tank for collecting the refined product, connected to the condenser through a conduit, which are formed from a stainless steel, and thus the evaporated and condensed fraction of the dihydroxyaryl compound is brought into contact with the inside surfaces of the condenser, conduit and collecting tank, formed from the stainless steel. In this case, the refined dihydroxyaryl compound is contaminated with impurity metals eluted from the stainless steel surface with which the refined dihydroxyaryl compound comes into contact.

SUMMARY OF THE INVENTION

An object of the present invention is to provide a method of refining a dihydroxyaryl compound, in which contamination of the refined dihydroxyaryl compound with impurity metals can be decreased and thus the resultant refined dihydroxyaryl compound has a high degree of purity.

The above-mentioned object can be attained by the method of the present invention for refining a dihydroxyaryl compound, which comprises; evaporating a dihydroxyaryl compound in a distillation column; condensing the resultant vapor fraction of the dihydroxyaryl compound in a condenser connected to a top outlet of the distillation column; and collecting the condensed dihydroxyaryl compound fraction into a storage tank through a conduit connected to an outlet of the condenser, wherein the condenser has an inside surface thereof formed from a metal material containing at least 25% by weight of nickel, and the condensed dihydroxyaryl compound fraction comes into contact with the nickel-containing metal material inside surface.

In the refining method of the present invention, at least one member of the conduit and the storage tank has an inside surface formed from a metal material containing at least 25% by weight of nickel.

In the refining method of the present invention, the nickel containing metal material comprises 25% by weight or more of nickel and 75% by weight or less of at least one member selected from the group consisting of chromium, molybdenum, tungsten, iron, silicon, copper and aluminum.

In the refining method of the present invention, the collected dihydroxyaryl compound fraction has a degree of purity of 99.9% or more, as determined by gas chromatographic analysis.

In the refining method of the present invention, the collected dihydroxyaryl compound fraction has a total metal content of 200 ppb or less.

In the refining method of the present invention, the dihydroxyaryl compound is selected from the group consisting of catechol, resorcinol, hydroquinone, 3-methylcatechol, 4-methylcatechol, 2-methylhydroquinone, 2-chlorcatechol and 4-chlorocatechol.

In the refining method of the present invention, the evaporating procedure is carried out at a temperature of the top outlet of the distillation column of 120 to 220° C. under an absolute pressure of 1 to 50 kPa.

In the refining method of the present invention, the nickel-containing metal material inside surface is treated with hot water or water steam before or during the refining procedure.

In the refining method of the present invention, the evaporation procedure is suspended and then the hot water or water steam treatment is applied to the nickel-containing metal material inside surface.

In the refining method of the present invention, the hot water or water steam treatment is applied to the nickel-containing metal material inside surface, while the evaporating procedure for the dihydroxyaryl compound is continued.

In the refining method of the present invention, the hot water treatment is effected at a hot water temperature of 40 to 150° C.

In the refining method of the present invention, the water steam is generated from a mixture of the dihydroxyaryl compound with water in an amount of 0.01 to 1% by weight based on the weight of the dihydroxyaryl compound contained in the distillation column.

The refined dihydroxyaryl compound of the present invention is produced by the method of the present invention and has a degree of purity of 99.9% or more, as determined by gas chromatographic analysis.

The refined dihydroxyaryl compound of the present invention is produced by the method of the present invention and has a total metal content of 200 ppb or less.

The dihydroxyaryl compound of the present invention has a degree of purity of 99.9% or more, as determined by gas chromatographic analysis.

The dihydroxy compound of the present invention has a total metal content of 200 ppb or less.

DESCRIPTION OF THE PREFERRED EMBODIMENTS

The refined dihydroxyaryl compound produced by the refining method of the present invention preferably has a restricted total content of impurity metals of 200 ppb or less, more preferably 100 ppb or less, as determined by an induced bond plasma meter and/or a flameless atomic absorption spectrometer. Also, the refined dihydroxyaryl compound prepared by the refining method of the present invention preferably has a degree of purity of 99.9% or more, as determined by gas-chromatography and calculated as an area percentage.

The impurity metals which may be contained in the refined dihydroxyaryl compound include iron, nickel, molybdenum, and chromium.

The dihydroxyaryl compound which is subjected to the refining method of the present invention is in the state of a liquid under the ambient atmospheric conditions and is preferably selected from the group consisting of dihydroxyaryl compounds free from alkyl groups, for example, catechol, resorcinol and hydroquinone; dihydroxy compounds having one or more alkyl groups, for example, 3-methylcatechol, 4-methylcatechol and 2-methylhydroquinone; and dihydroxyaryl compounds further substituted with one or more halogen atoms, for example, 3-chlorocatechol or 4-chlorocatechol, more preferably catechol. There is no limitation to the degree or purity of or the type of impurity metals contained in the dihydroxyaryl compound. Usually, the dihydroxyaryl compound, for example, catechol, having a degree of purity of 99% or more, and containing about 500 ppb of iron, about 100 ppb of nickel, about 150 ppb of chromium and about 50 ppb of molybdenum is subjected to the refining method of the present invention.

The distillation column of the distillation apparatus usable for the refining method of the present invention is not limited to a specific type of distillation column and may be selected from conventional evaporator type distillation columns, packed column type distillation columns, and tray type distillation columns, generally the packed column type distillation columns each having at least a condenser having an inside surface formed from a Ni-containing metal. The packing materials for the packed column type distillation columns are selected from trade-available packing materials, preferably, for example, pall rings made from, for example, stainless alloys or Ni—Mo—Fe alloys, for example, HASTELLOY A, B and C (registered trademark), THROUSER (registered trademark) packings (made from a stainless steel), MELAPACK (registered trademark), MELACARBON (registered trademark, made from a carbon), and MELAJUL (registered trademark, made from a ceramic).

The packing materials are usually packed in two or more theoretical plate numbers, to prevent a contamination of the evaporated fraction generated in the distillation column with flush accompanied from the bottom of the distillation column.

In the refining method of the present invention, the starting dihydroxyaryl compound is evaporated in the distillation column, the resultant vapor fraction is condensed in a condenser connected to a top outlet of the distillation column and the condensed dihydroxyaryl compound fraction is collected into a storage tank through a conduit connected to an outlet of the condenser. In the distillation apparatus, the condensed fraction comes into contact with the inside surfaces of the condenser, the storage tank and the conduit through which the condenser is connected to the storage tank.

In the refining method of the present invention, at least the condenser has an inside surface thereof formed from a metal material containing at least 25% by weight of nickel. When the dihydroxyaryl compound vapor fraction is condensed in the condenser, the condensed fraction first comes into contact with the inside surface of the condenser.

The nickel-containing metal material contains 25% by weight or more, preferably 30% by weight or more, of nickel. Preferably, the nickel-containing metal material is selected from alloys comprising 25% by weight or more, more preferably 30% by weight or more, of nickel and 75% by weight or less, more preferably 70% by weight or less of at least one metal selected from chrominum, molybdenum, tungsten, iron, silicon, copper and aluminum, preferably chrominum, molybdenum, tungsten and iron.

The inside surfaces of the storage tank and the conduit may be formed from a metal material other than the nickel-containing metal material as defined above. However, optionally, at least one of the inside surfaces of the storage tank and the conduit is formed from the metal material containing at least 25% by weight or more of nickel.

The nickel alloys usable for forming the inside surfaces of at least the condenser and optionally of the storage tank and the conduit are preferably selected from alloys of nickel with chrominum, molybdenum, tungsten and iron, for example HASTELLOY (registered trademark) A, B, and C (made by HAYNES STELLITE CO.) and CARPENTER (registered trademark).

The specific nickel-containing metal material forming the inside surface of the condenser and optionally the storage tank and/or the conduit is contributory to enhancing the degree of the purity of the refined dihydroxyaryl compound to 99.9% or more, and to decreasing total content of the impurity metals to 200 ppb or less, preferably 100 ppb or less.

In the refining method of the present invention, the starting dihydroxyaryl compound is fed into a bottom portion of the distillation column and evaporated at a column top temperature of 120 to 220° C., preferably 120 to 200° C. under an absolute distillation pressure of 1 to 50 kPa, preferably 1 to 25 kPa.

The resultant vapor fraction of the dihydroxyaryl compound is delivered through a top outlet of the distillation column and introduced into a condenser connected to the top outlet of the distillation column, and condensed in the condenser. The resultant condensed liquid fraction of the dihydroxyaryl compound is delivered from the condenser through an outlet thereof and then introduced into a storage tank through a conduit. The condensed liquid fraction of the dihydroxyaryl compound first comes into contact with the inside surface of the condenser and successively with the inside surfaces of the conduit and the storage tank.

The above-mentioned refining procedures may be carried out in a batch-type or continuous distillation apparatus.

In an initial stage of the refining procedure in accordance with the method of the present invention, the resultant refined dihydroxyaryl compound has a very low total content of the impurity metals of 200 ppb or less, preferably 100 ppb or less. However, the total content of the impurity metals may increase with the lapse of the refining procedure time. Namely, when the distillation procedure is repeatedly carried out in the distillation apparatus, preferably the inside surface of the condenser and optionally the inside surfaces of the conduit and/or the storage tank is treated with hot water or water steam. In the hot water treatment, the hot water is brought into contact with the target inside surface or surfaces. In the water steam treatment, the water steam is brought into contact with the target inside surface or surfaces. When no hot water or water steam treatment is applied to the nickel containing metal inside surface over a long period, the total content of the impurity metals in the resultant refined dihydroxyaryl compound may reach a level of 200 ppb and then may exceed the level.

The hot water treatment is carried out, for example, by suspending the distillation procedure, and then by feeding the hot water through a conduit connected to a conduit through which the top outlet of the distillation column is connected to an inlet of the condenser at a location immediately upstream of the inlet of the condenser, into the inside of the condenser, by allowing the hot water to flow through the condenser, and by discharging the hot water through a discharge conduit connected to the conduit between the condenser and the storage tank at a location immediately upstream of the storage tank. The hot water treatment is carried out under an increased pressure or a reduced pressure. The hot water treatment temperature is preferably 40 to 150° C., more preferably 50 to 100° C.

The water steam treatment can be carried out, for example, by suspending the distillation procedure and then by feeding, flowing through the condenser and discharging the water steam in the same manner as in the hot water treatment. Alternatively, while the distillation procedure is continued, the water steam is fed, flowed through the condenser and discharged in the same manner as in the hot water treatment. The water steam treatment is carried out under an increased pressure or a reduced pressure. The temperature of the water steam is set in response to the treatment pressure and is preferably in the range of 50 to 170° C., more preferably 100 to 150° C.

In the water steam treatment which is applied after the distillation procedure is suspended, for example, (a) the starting dihydroxyaryl compound is completely withdrawn from the distillation column, water is fed into the distillation column through a feed inlet for the starting dihydroxyaryl compound, and is evaporated, and the generated water steam is allowed to flow into the condenser and condensed therein to reflux; or (b) while maintaining the starting dihydroxyaryl compound within the distillation column, water steam is blown into the distillation column through the feed inlet for the starting dihydroxyaryl compound, is allowed to flow through the condenser, and is finally discharged through a discharge conduit connected to the conduit through which the condenser is connected at a location immediately upstream to the storage tank; or (c) the refined dihydroxyaryl compound is withdrawn from the storage tank, while the starting dihydroxyaryl compound is retained in the distillation column, and water steam is blown into the distillation column through a feed inlet for the starting dihydroxyaryl compound, is allowed to flow through the condenser, the conduit and the storage tank and then discharged through a discharged conduit connected to the storage tank.

Also, in the water steam treatment which is carried out while the distillation procedure is continued, for example, a small amount of water is mixed into the starting dihydroxyaryl compound, the water is vaporized together with the dihydroxyaryl compound and the water steam is brought into contact with the inside surface of the condenser. The amount of the mixed water is preferably 0.01 to 1% by weight based on the weight of the starting dihydroxyaryl compound.

EXAMPLES

The present invention will be further illustrated by the following examples which are not intended to limit the scope of the present invention in any way.

In the following examples and comparative examples, gas chromatographic analysis was carried out under the following conditions.

Gas chromatographic analysis conditions
Detector: Hydrogen flame ionization detector
Column: Silicon OV-17 (Chromosorb WAW-DMCS), 3 mm$\phi$×3 m
Column temperature: 200° C.
Inlet temperature: 250° C.
Detector temperature: 250° C.
Carrier gas: Helium
Flow rate: 50 ml/min The degree of purity of the dihydroxyaryl compound was calculated as an area percentage in the gas chromatographic analysis.

Example 1

A distillation apparatus comprising a packed type distillation column having a diameter of about 250 cm and a height of 4 m and packed with Pall rings (formed from a nickel alloy (HASTELLOY (registered trademark) C); a condenser having a heat transfer area of 2 m$^2$, and connected to a top outlet of the distillation column; a storage tank; and a conduit through which an outlet of the condenser is connected to an inlet of the storage tank, the condenser, the conduit and the storage tank being formed from a nickel alloy (HASTELLOY (registered trademark) C), was employed. The nickel alloy (HASTELLOY C) comprised 54.5 to 59.5% by weight of Ni, 15 to 19% by weight of Mo, 0.04 to 0.15% by weight of C, 4 to 7% by weight of Fe, 1.3 to 1.6% by weight of Cr and 3.5 to 5.5% by weight of W.

A starting trade catechol having a degree of purity of 99.0% or more, and containing 500 ppb of Fe, 100 ppb of Ni, 150 ppb of Cr and 50 ppb of Mo, was fed in an amount of 50 kg into the bottom portion of the distillation column, and was heated up to a temperature of 185° C. by passing steam through a heating coil arranged within the bottom portion of the distillation column, under a reduced absolute pressure of 14 kPa to distill the starting catechol at a reflux ratio of 0.5. The resultant catechol vapor fraction was cooled and condensed in the condenser connected to the top outlet of the distillation column, and the condensed catechol fraction was delivered from the condenser and collected in an amount of 37 kg in the storage tank through the conduit. During the distillation, condensing and collecting procedures, the condensed catechol fraction came into contact with the nickel alloy (HASTELLOY C) inside surfaces of the condenser, the conduit and the storage tank.

The resultant refined catechol was subjected to the gas chromatographic analysis. It was confirmed that the degree of purity of the refined catechol was 99.9% or more.

Also, the refined catechol was subjected to a measurement of impurity metal content by using an inductive bond plasma measurement apparatus and a flameless atomic absorption spectrometer. It was confirmed that the refined catechol contained 3 ppb of Fe, 8 ppb of Ni, 2 ppb of Mo and 2 ppb of Cr. The total content of the impurity metals was 15 ppb.

Comparative Example 1

The same starting catechol as in Example 1 was refined by the same procedures as in Example 1, except that the distillation column, the condenser, the conduit and the storage tank were formed from a stainless steel (SUS 316L, made by NISSHIN SEIKO K.K.). The resultant refined catechol was subjected to the same analyses as in Example 1. The refined catechol has a degree of purity of 99.9% or more and contained 420 ppb of Fe, 59 ppb of Ni, 10 ppb of Mo and 103 ppb of Cr.

The total content of impurity metals was 592 ppb.

Example 2

The refining procedure of Example 1 was followed by the continuous refining procedure in which the same trade catechol having a degree of purity of 99% or more and containing 500 ppb of Fe, 100 ppb of Ni, 150 ppb of Cr and 50 ppb of Mo was fed into the bottom portion of the distillation column at a feed rate of 80 kg/hr and distilled, condensed and collected, continuously, for 100 hours under the same conditions as in Example 1. During the distillation procedure, the liquid catechol fraction in the bottom portion of the distillation column was not withdrawn. After the continuous 100 hour distillation, the collected refined catechol had a degree of purity of 99.9% or more and contained 5 ppb of Fe, 13 ppb of Ni, 3 ppb of Mo and 4 ppb of Cr, determined by the same measurements as in Example 1.

Further, the same continuous distillation procedure as mentioned above was carried out for another 100 hours. The resultant collected refined catechol contained 7 ppb of Fe, 27 ppb of Ni, 5 ppb of Mo and 3 ppb of Cr, determined by the same measurements as in Example 1.

Still further, the same continuous distillation procedure as mentioned above was carried out for another 100 hours. The resultant collected refined catechol had a degree of purity of 99.9% or more and contained 11 ppb of Fe, 39 ppb of Ni, 9 ppb of Mo and 10 ppb of Cr, determined by the same measurements as in Example 1.

After the continuous 300 hour distillation was finished, the feeding of the starting catechol was stopped, and the temperature of the inside of the distillation apparatus was reduced to room temperature while the pressure of the inside of the distillation apparatus was maintained under the distillation pressure, without withdrawing the liquid catechol fraction in the distillation column. Then, water steam under a gauge pressure of 0.4 MPa was fed into the distillation column through the feed inlet for the starting catechol at a feed rate of 10 kg/hr; was allowed to flow through the condenser and the conduit; and was discharged through a conduit connected to the conduit between the condenser and the storage tank at a location immediately upstream to the storage tank, over a period of 2 hours.

Thereafter, the same continuous distillation procedure for the same starting catechol as those mentioned above was carried out for 10 hours using the water steam-treated distillation apparatus.

The resultant refined catechol contained 4 ppb of Fe, 13 ppb of Ni, 3 ppb of Mo and 4 ppb of Cr, determined by the same measurements as in Example 1.

Further, the same continuous distillation procedure for the same starting catechol as those mentioned above was carried out for 350 hours. The resultant refined catechol had a degree of purity of 99.9% or more and contained 11 ppb of Fe, 37 ppb of Ni, 8 ppb of Mo and 10 ppb of Cr, determined by the same measurements as in Example 1, the total content of the impurity metals being 66 ppb.

Example 3

The continuous distillation procedures of Example 2 were followed by the further continuous distillation procedures as stated below.

The same starting catechol as mentioned in Example 1 (having a degree of purity of 99% or more and containing 500 ppb of Fe, 100 ppb of Ni, 150 ppb of Cr and 50 ppb of Mo) was continuously fed in a feed rate of 80 kg/hr into the bottom portion of the distillation column and distilled, condensed and collected under the same conditions as in Example 1 for 300 hours.

The resultant refined catechol had a degree of purity of 99.9% or more and contained 27 ppb of Fe, 133 ppb of Ni, 18 ppb of Mo and 25 ppb of Cr, determined by the same measurements as in Example 1, the total impurity metal content being 203 ppb.

Then, the distillation procedure was interrupted, and the same water steam treatment as in Example 2 was applied to the distillation apparatus. Thereafter, the same continuous distillation procedure was carried out under the same conditions as in Examples for 10 hours.

The resultant refined catechol had a degree of purity of 99.9% or more and contained 5 ppb of Fe, 12 ppb of Ni, 2 ppb of Mo and 4 ppb of Cr, determined by the same measurements as in Example 1, the total impurity metals being 23 ppb.

The refining method of the present invention for a dihydroxyaryl compound contributes to enhancing the degree of purity and to significantly reducing the contents of impurity metals, for example, iron, nickel, chromium and molybdenum. Particularly, since catechol can form chelate compounds with various metals and thus is useful as a cleaning agent for removing various metals contaminating base plates for electronic devices, the refining method of the present invention is advantageously applied to the production of catechol having a high degree of purity and a significantly reduced impurity metal content.

What is claimed is:

1. A method of refining a dihydroxyaryl compound, comprising:

evaporating a dihydroxyaryl compound in a distillation column, wherein a top outlet of the distillation column is connected to a condenser;

suspending said evaporation step and applying a hot water or steam treatment to the inside surface of the condenser;

condensing the resultant vapor fraction of the dihydroxyaryl compound in said condenser so that the condensed dihydroxyaryl compound comes into contact with said inside surface of the condenser; and collecting the condensed dihydroxyaryl compound fraction into a storage tank through a conduit connected to an outlet of the condenser;

wherein the condenser has an inside surface thereof formed from a metal material comprising at least 25% by weight nickel.

2. The refining method as claimed in claim 1, wherein at least one member of the conduit and the storage tank has an inside surface formed from a metal material containing at least 25% by weight of nickel.

3. The refining method as claimed in claim 1, wherein the nickel-containing metal material comprises at least 25% by weight nickel and at most 75% by weight of at least one member selected from the group consisting of chromium, molybdenum, tungsten, iron, silicon, copper and aluminum.

4. The refining method as claimed in claim 1, wherein the collected dihydroxyaryl compound fraction has at least a 99.9% degree of purity, determined by a gas chromatographic analysis.

5. The refining method as claimed in claim 1, wherein the collected dihydroxyaryl compound fraction has a total metal content not exceeding 200 ppb.

6. The refining method as claimed in claim 1, wherein the dihydroxyaryl compound is selected from the group consisting of catechol, resorcinol, hydroquinone, 3-methylcatechol, 4-methylcatechol, 2-methylhydroquinone, 2-chlorocatechol and 4-chlorocatechol.

7. The refining method as claimed in claim 1, wherein the evaporating procedure is carried out at a temperature of the top outlet of the distillation column of 120 to 220° C. under an absolute pressure of 1 to 50 kPa.

8. The refining method as claimed in claim 1, wherein the hot water treatment is effected at a hot water temperature of 40 to 150° C.

9. The refining method as claimed in claim 1, wherein the steam is generated from a mixture of the dihydroxyaryl compound with water in an amount of 0.01 to 1% by weight based on the weight of the dihydroxyaryl compound contained in the distillation column.

10. A method of refining a dihydroxyaryl compound, comprising:

evaporating a dihydroxyaryl compound in a distillation column, wherein a top outlet of the distillation column is connected to a condenser;

applying a hot water or steam treatment to the inside surface of the condenser while said evaporation step is continued;

condensing the resultant vapor fraction of the dihydroxyaryl compound in said condenser so that the condensed dihydroxyaryl compound comes into contact with said inside surface of the condenser; and collecting the condensed dihydroxyaryl compound fraction into a storage tank through a conduit connected to an outlet of the condenser;

wherein the condenser has an inside surface thereof formed from a metal material comprising at least 25% by weight nickel.

11. The refining method as claimed in claim 10, wherein the collected dihydroxyaryl compound fraction has at least a 99.9% degree of purity, determined by a gas chromatographic analysis.

12. The refining method as claimed in claim 10, wherein the collected dihydroxyaryl compound fraction has a total metal content not exceeding 200 ppb.

13. The refining method as claimed in claim 10, wherein the dihydroxyaryl compound is selected from the group consisting of catechol, resorcinol, hydroquinone, 3-methylcatechol, 4-methylcatechol, 2-methylhydroquinone, 2-chlolorcatechol and 4-chlorocatechol.

14. A method of refining a dihydroxyaryl compound, comprising:

applying a hot water or steam treatment to the inside surface of a condenser connected to a top outlet of a distillation column;

evaporating a dihydroxyaryl compound in the distillation column, said evaporation step occurring after the hot water or steam treatment step;

condensing the resultant vapor fraction of the dihydroxyaryl compound in said condenser so that the condensed dihydroxyaryl compound comes into contact with said inside surface of the condenser; and collecting the condensed dihydroxyaryl compound fraction into a storage tank through a conduit connected to an outlet of the condenser;

wherein the condenser has an inside surface thereof formed from a metal material comprising at least 25% by weight nickel.

15. The refining method as claimed in claim 14, wherein the collected dihydroxyaryl compound fraction has at least a 99.9% degree of purity, determined by a gas chromatographic analysis.

16. The refining method as claimed in claim 14, wherein the collected dihydroxyaryl compound fraction has a total metal content not exceeding 200 ppb.

17. The refining method as claimed in claim 14, wherein the dihydroxyaryl compound is selected from the group consisting of catechol, resorcinol, hydroquinone, 3-methylcatechol, 4-methylcatechol, 2-methylhydroquinone, 2-chlorcatechol and 4-chlorocatechol.

* * * * *